(12) United States Patent
Liungman

(10) Patent No.: US 8,535,371 B2
(45) Date of Patent: Sep. 17, 2013

(54) METHOD OF POSITIONING A TUBULAR ELEMENT IN A BLOOD VESSEL OF A PERSON

(75) Inventor: Krister Liungman, Uppsala (SE)

(73) Assignee: Endovascular Development AB, Uppsala (SE)

( * ) Notice: Subject to any disclaimer, the term of this patent is extended or adjusted under 35 U.S.C. 154(b) by 216 days.

(21) Appl. No.: 12/946,377

(22) Filed: Nov. 15, 2010

(65) Prior Publication Data

US 2012/0123510 A1    May 17, 2012

(51) Int. Cl.
*A61F 2/07*    (2013.01)
*A61F 2/06*    (2006.01)

(52) U.S. Cl.
USPC .......................................... 623/1.35; 623/1.11

(58) Field of Classification Search
USPC ................... 623/1.11, 1.35; 606/108
See application file for complete search history.

(56) References Cited

U.S. PATENT DOCUMENTS

| | | | |
|---|---|---|---|
| 6,179,859 B1 * | 1/2001 | Bates et al. | 606/200 |
| 6,355,051 B1 | 3/2002 | Sisskind et al. | |
| 6,371,971 B1 | 4/2002 | Tsugita et al. | |
| 6,607,555 B2 * | 8/2003 | Patterson et al. | 623/1.23 |
| 6,814,752 B1 * | 11/2004 | Chuter | 623/1.35 |
| 6,969,395 B2 | 11/2005 | Eskuri | |
| 7,316,655 B2 | 1/2008 | Garibotto et al. | |
| 7,776,062 B2 | 8/2010 | Besselink et al. | |
| 2002/0065545 A1 * | 5/2002 | Leonhardt et al. | 623/1.1 |
| 2003/0199967 A1 * | 10/2003 | Hartley et al. | 623/1.13 |
| 2004/0098079 A1 * | 5/2004 | Hartley et al. | 623/1.11 |
| 2005/0113862 A1 | 5/2005 | Besselink et al. | |
| 2005/0203569 A1 | 9/2005 | Kusleika et al. | |
| 2006/0129180 A1 | 6/2006 | Tsugita et al. | |
| 2007/0162071 A1 | 7/2007 | Burkett et al. | |
| 2008/0119889 A1 * | 5/2008 | Kusleika | 606/200 |
| 2009/0326550 A1 | 12/2009 | Drake et al. | |
| 2009/0326551 A1 | 12/2009 | Drake et al. | |
| 2009/0326629 A1 | 12/2009 | Drake et al. | |
| 2009/0326630 A1 | 12/2009 | Tobin et al. | |
| 2010/0152769 A1 | 6/2010 | Gesswein et al. | |
| 2011/0270385 A1 * | 11/2011 | Muzslay | 623/1.35 |

FOREIGN PATENT DOCUMENTS

| | | |
|---|---|---|
| CA | 2613117 C | 5/2001 |
| EP | 1847234 A1 | 10/2007 |
| EP | 2 065 015 A1 | 6/2009 |
| JP | 9-173466 A | 7/1997 |
| WO | WO 2005/037141 A2 | 4/2005 |
| WO | WO 2005/105191 A2 | 11/2005 |
| WO | WO 2007/124053 A1 | 11/2007 |
| WO | WO 2008/022262 A1 | 2/2008 |
| WO | WO 2008/112270 A1 | 9/2008 |
| WO | WO 2009/158444 A1 | 12/2009 |

* cited by examiner

*Primary Examiner* — Gary Jackson
*Assistant Examiner* — Richard Louis
(74) *Attorney, Agent, or Firm* — Foley & Lardner LLP

(57) ABSTRACT

A method of positioning a tubular element inside a main blood vessel of a person. The tubular element has a main tube with one or more side openings and a transport wire extending through each side opening. A fixator being positioned in each branch vessel and the corresponding guide wire being attached to the corresponding transport wire, whereby re-routing of the guide wire is performed by pulling the transport wire to have the guide wire extend from the fixator through the corresponding side opening and to the outside of the person. This re-routed guide wire may be used for positioning the tubular element or guiding additional elements from the tubular element and into the branch vessel.

12 Claims, 10 Drawing Sheets

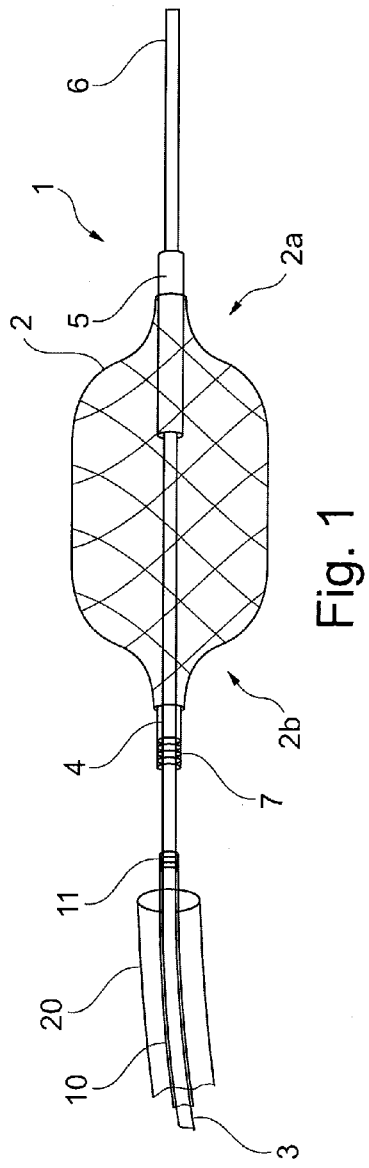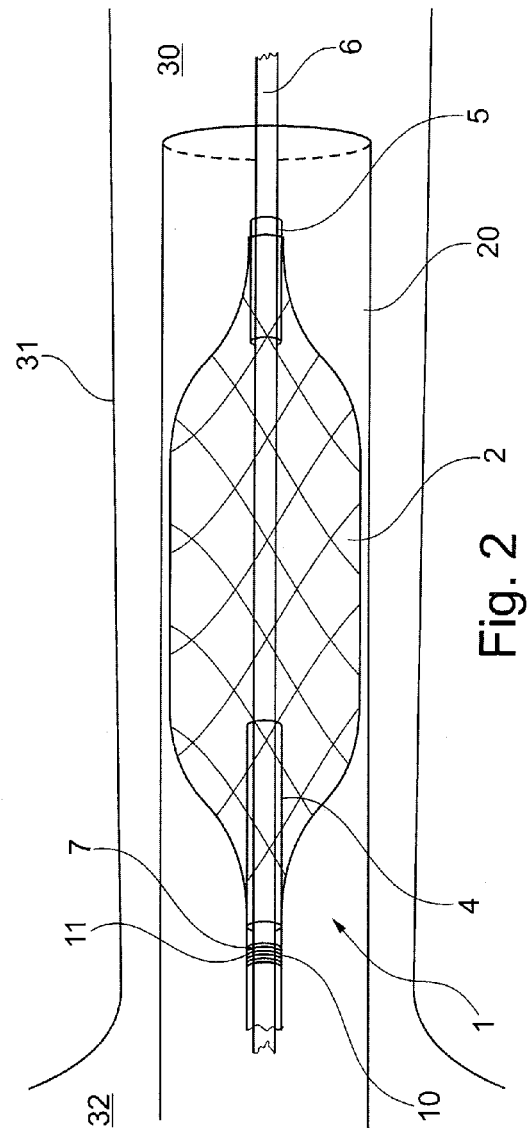
Fig. 1
Fig. 2

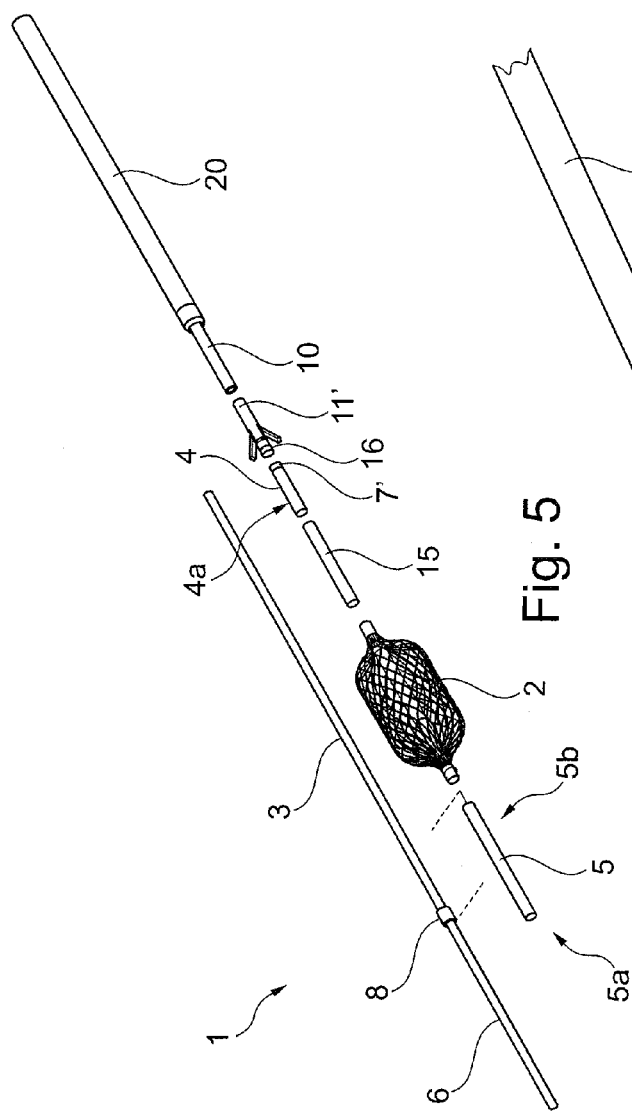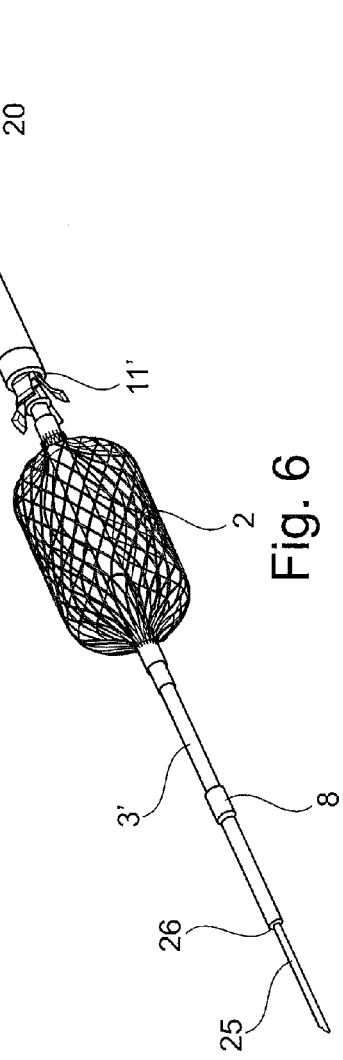

METHOD OF POSITIONING A TUBULAR ELEMENT IN A BLOOD VESSEL OF A PERSON

The present invention relates to a method of positioning a tubular element in a blood vessel of a person and more particularly a manner of positioning a fenestrated, branched or multiple branch stent graft in a person.

The use of graft stents in persons is a routine technique for alleviating e.g. aneurisms which could otherwise burst and cause massive internal bleedings and death. The grafts, when positioned, form internal walls or structures in the blood vessels and thus alleviate the pressure causing and bursting the aneurisms.

BACKGROUND OF THE INVENTION

The positioning of a fenestrated or branched graft is difficult in that the opening into the branch vessel in which the branch of the graft is to be positioned may be more or less clogged, may be positioned differently from person to person, and the branch vessel may be angled, relative to the main vessel, differently from person to person.

SUMMARY OF THE INVENTION

Thus, when positioning the graft inside the main vessel, it is difficult to have the graft branch or side opening direct or extend directly toward the branch vessel and/or into this branch vessel. If the graft branch is positioned a bit off or angled a bit off, it is extremely difficult to direct the graft opening or branch toward or into the vessel branch.

One solution to the positioning/angling has been to perform detailed tomography of the blood vessels of the person and produce individualized branched grafts for each person. Such grafts, however, are extremely expensive and do not solve the difficulties caused by extensive blood clogging in the aneurisms. Also, the rotational positioning thereof, to have the branches point toward the respective branch vessels, is based on making two markings on opposite sides of the graft overlap.

In a first aspect, the invention relates to a method of positioning a tubular element having:
  a main tube having an inner space defined between a first and a second end portion along a longitudinal axis of the main tube and at least an end opening at the first end portion from the inner space to surroundings of the main tube,
  a side opening positioned between the first and second end portions between the inner space and the surroundings,
  a transport wire having a first part, which extends from the inner space and out of the tubular element through the end opening, and a second part, which extends from the inner space and out of the tubular element through the side opening,
in a main blood vessel, having a branch vessel, of a person or animal, the method comprising:
  providing an assembly having a guide wire and a fixator adapted to be releasably attached to an inner side of the branch vessel, the fixator being attached to the guide wire, which guide wire has a distal end for introduction into the branch vessel and a proximal end,
  introducing the fixator into the branch vessel, via the main blood vessel, and fixing the fixator to the branch vessel,
  providing the tubular element inside the main blood vessel so that the first part of the transport wire is engageable from outside the patient,
  fixing or attaching the second part of the transport wire to the guide wire, and
  pulling the first part of the transport wire to have the guide wire extend from the fixator through the side opening, the inner volume, and the end opening.

In this context, a tubular element is a hollow element having an internal space or volume and openings between the internal volume and the surroundings of the tubular element. In this context, the surroundings is the space or volume outside the tubular element not forming part of the internal volume.

The tubular element extends along a longitudinal axis which may be straight, bent, curved or have any shape which may depend on or be defined by e.g. the shape of the main blood vessel (see further below).

Preferably, the main tube has a wall defining an end opening at each end portion and through which the longitudinal axis extends, where the side opening is formed in the wall so as to open is into the main volume from a lateral position or angle, i.e. an angle not identical to the longitudinal axis at the longitudinal position of the side opening. As will be made clear further below, the tubular element may have any number of side openings. The side opening(s) may be positioned at any position in the main tube and in relation to any other side opening(s).

The tubular element may comprise means for fastening the main tube to the main blood vessel of the person if desired. Such means may be hook like or spike like elements for travelling into a wall of the blood vessel or may be expanding elements or hook like elements adapted to expand and/or engage the inner side of the blood vessel, such as irregularities thereof.

Usually, the tubular element will resemble, mimic or copy the structure and overall shape of the main vessel. However, the tubular element may have a smaller cross section, perpendicular to a longitudinal axis thereof, in order to e.g. treat aneurisms, for example, which increase the blood vessel cross section. Then, the positions of the side opening(s) may preferably correspond to the position(s) the branch vessel(s) in order for blood, subsequent to the deployment of the tubular element, to be able to flow from the inner volume and into the branch vessel(s).

Preferably, the tubular element is formed of a material which is at least substantially impermeable to blood, as it may have a desired function of forming a new blood vessel or at least forming an inner, pressure reducing, element in a blood vessel. Thus, preferably, blood flow from the surroundings (when deployed) of the tubular element and into the inner volume is possible only via the openings.

The tubular element may be collapsible and/or expandable in order to be more easily positioned within the blood vessel(s) of the person/animal.

The transport wire and the guide wire may be any type of wire adapted to (or useful for) be introduced into a blood vessel of a person. Presently, a guide wire and/or transport wire is an elongated element adapted to be introduced into a blood vessel of a person. Often, a guide/transport wire has a slippery surface, such as a hydrophilic surface, so as to be introduced into the blood vessel without harming the vessel. Typical guide/transport wires for catheterization have a circumference of between 0.14 and 0.89 mm. However, any thickness may in principle be used. The guide/transport wire may be made of a polymer or a metal/alloy, such as nitinol.

The guide wire may be of a type having an outer sleeve which is rather pliable and an inner, stiffer, element which may be introduced into the sleeve, when the guide wire is desired more stiff and which may be withdrawn, when the guide wire is desired more pliable.

According to the invention, the transport wire has a first part extending from inside the main tube and out of the tubular element through the end opening and a second part extending from the inner volume and out of the tubular element through the side opening. Thus, the transport wire may preferably be pulled out from the tubular element by puling any of the first and second parts. Preferably, the transport wire is a single, longitudinal element.

In the present context, the main blood vessel preferably denotes the larger of the main blood vessel and the branch vessel. In many situations, the blood vessels are arteries, where the main blood vessel then provides blood flow toward and into the branch vessel.

Usually, the present fixator is for use in arteries of the person/animal, such as the aorta or one of the arteries directly receiving blood from the aorta, but this is not a limitation. Thus, in one situation, the main blood vessel is the aorta of a person, where the branch vessel may then be the visceral arteries and the aortic arc arterial branches. In other situations, the method may be used in the common iliac artery, and the internal iliac arteries.

In this context, the distal end of the guide wire is that intended to be introduced into the blood vessel, whereas the proximal end is intended to extend away from the branch vessel and in some embodiments (see further below) out of the person. Thus, the proximal end may also extend into or be provided inside the blood vessel of the person but will then be the end introduced the latest or the end being closest, along the blood vessels, to the user/surgeon.

In the present context, the fixator is brought to fix/engage or attach itself to the blood vessel in any desirable manner. A preferred manner is a friction attachment by which the fixator purely by friction attaches the blood vessel and thereby counteracts removal thereof along the axis of the blood vessel. A typical manner of obtaining a friction engagement is to have the providing step comprise providing the fixator inside the blood vessel in a collapsed form and thereafter allow the fixator to expand so as to contact the inner side of the blood vessel. Usually, an expanding fixator will expand to be limited by the inner dimensions of the blood vessel so as to exert a predetermined force to the inner side of the blood vessel to stay in place.

Naturally, also other manners of engaging or, attaching to the blood vessel are known, such as elements with small spikes or nails which travel into the blood vessel wall in order to maintain the element in the desired position.

Preferably, the fixing/attaching/engaging of the fixator to the vessel wall is a releasable attachment so that the fixator may be repositioned or removed (see further below) during or after the procedure.

The step of providing the tubular element inside the main blood vessel may comprise providing the tubular element therein in a fully collapsed or partly collapsed state, such as a state in which a cross sectional area or circumference thereof, perpendicular to the longitudinal axis, is smaller than in a fully deployed state, which is the final state which the tubular element is to maintain in the blood vessel. In this situation, it may be desired to position the tubular element before fully deploying it. This positioning may be a positioning along the longitudinal axis or along the main blood vessel as well as a rotational positioning in order to have the side opening correspond, in position, to the branch vessel or at least an opening thereof into the main vessel. When the tubular element is in the fully deployed state, it may contact the vessel walls of the main vessel and thus be more difficult to reposition.

This positioning of the tubular element may be performed during the pulling step or after the pulling step by exerting a force to the guide wire so as to force the side opening toward the branch vessel in which the fixator is fixed.

Having thus positioned the tubular element, the method may comprise, pursuant to the pulling step, bringing the tubular element from the fully or partly collapsed state and to a fully deployed state in order to e.g. fix the tubular element inside the main vessel.

Such tubular elements may be introduced into a blood vessel in a collapsed state while guided by a guiding catheter, brought to a partly collapsed state while engaged or maintained in the partly collapsed state, such as by the guiding catheter, and positioned, before being released from the guiding catheter and allowed to obtain the fully deployed state.

Having provided the tubular element within the main vessel, the first part is engageable from outside the patient. In a preferred embodiment, the first part extends to the outside of the patient, usually through a percutaneous arterial puncture, but if positioned inside a blood vessel of the patient, it is still accessible for e.g. snaring using another guide wire or a snaring catheter. This is standard procedure for endovascular surgeons.

The attachment of the guide wire to the fixator may be permanent or releasable. Further below, a releasable attachment or restraining is described which has a number of advantages.

The fixing or attaching of the second part of the transport wire to the guide wire may be an attachment of any type, such as a if one of the second part and the guide wire has a hook and the other a loop, or if one of the second part and the guide wire has a claw or the like adapted to engage, fix or grab the other, or, for example, if one of the second part and the guide wire has a snare. Often a snare is provided on a wire which may be withdraw into a catheter so as to fix an element extending into the snare. Additionally, the two wires may be attached to each other using a third element, such as a clamp or the like, or they may simply be tied to each other by e.g. a knot. In fact, the attachment need not be a fixing. If e.g. the second part has a snare, it may be guided, such as by pulling the first part and fixing the proximal part of the guide wire. In this manner the snare will move toward the branch vessel and when being sufficiently close thereto, the proximal part of the guide wire may be released so that the pulling of the transport wire may re-route the guide wire which, due to the operation of the snare, will follow the snare to the outside of the person, as the snare slides along the guide wire as fixed by the fixator at the distal end thereof.

It is noted that a replacement of the transport wire with a subsequent wire, which is then pulled in order to re-track the guide wire will be tantamount to performing the same operation using the transport wire.

The pulling step may comprise any manner of transporting, withdrawing, translating or moving the first part of the transport wire and consequently the second part and the guide wire. Any means or method may be used for this movement, such as an engine, a translating element, a spring or the like. A simple manner would be for a surgeon or the like to pull the first part, if external to the person and otherwise engaged by another element, to obtain the overall result of the guide wire finally extending through the branch tube and the main tube (usually along the same path formerly occupied, by the transport wire). Thus, the guide wire may now be used for guiding elements through the main and branch tubes and into or toward the branch vessel.

The present tubular element may be a simple tubular element having merely holes therein, such as the elements usually denoted a fenestrated graft. Alternatively, the tubular element may have a main tube and one or more branch tubes, such as the so-called branched grafts.

Thus:

the tubular element may comprise a branch tube attached to the main tube and opening into the main tube, the side opening being an opening from the surroundings into the branch tube, and the second part of the transport wire then may extend from the inner volume of the main tube and out of the tubular element through the branch tube and the side opening.

In this context, the tubular element preferably has a main tube having, if having a circular cross section, a larger radius or, more generally, a larger cross section, than the branch tube, which may also have any desired cross section.

Preferably, the main tube and branch tube are assembled, such as fixed to each other, if not provided as a monolithic element, in a liquid (typically blood) impermeable manner, so that liquid (blood) is not able to escape from inside the main tube and to the surroundings of the tubular element through any interface there between. In addition, preferably, the main tube and the branch tube comprise at least essentially liquid (typically blood) impermeable walls in order to e.g. be adapted to alleviate a blood pressure to the walls of the main blood vessel, except via one of the openings of the main and branch tubes. Consequently, the tubular element preferably is at least substantially liquid impermeable except at the openings thereof.

One result of this is that the branch tube may now be directed toward or actually into the branch vessel, as it may be guided along the guide wire extending from the branch vessel and into the branch tube, during or after the pulling step. Exerting a force to the guide wire, subsequent or under the pulling step, may force the branch tube toward or into the branch vessel. Secondly, elements may subsequently be introduced into the branch vessel via the guide wire and the branch tube, such as when introducing a secondary tubular element intended to extend from the branch tube (such as be fixed to or engaging the branch tube) and into the branch vessel, such as further into the branch vessel than the branch tube, may be obtained by using the guide wire as a guide for the introduction of this secondary tube. This is described further below.

It is noted that if no branch tube is present, such as if a so-called fenestrated graft is used, it is also possible to provide a secondary tubular element which is guided by the guide wire and which then is attached to or engages the main tube, usually at the side opening. Then, the secondary tubular element may be flared in order to seal the side opening and so that it does not detach from the main tube and travel into the branch vessel.

In general, the guide wire preferably has a length sufficient for it to extend out of the person after the pulling step. Then, the transport wire can be pulled or moved to outside the patient/animal and may then be discarded. Alternatively, the guide wire may extend part of the path from the fixator to outside the patient and the transport wire, attached to the guide wire will extend the remainder of the path. In this situation, the combined/attached guide wire and transport wire may perform the subsequent guiding operation.

In one embodiment:

the introducing step comprises the step of having the guide wire of the fixed fixator extend to the outside of the person, the providing step comprises having also the second part of the transport wire extend to the outside of the patient, and the fixing/attaching step comprises fixing or attaching the second part to the guide wire outside the person.

This is a simple manner of obtaining a swift and secure fixing/attaching by performing it outside the body.

Especially in this situation, it is preferred that the introducing step comprises introducing the fixator into a blood vessel of a person through a percutaneous opening into a blood vessel, and wherein the providing step providing the tubular element inside the main blood vessel through the same opening of the person.

Alternatively, the fixing/attaching step may comprise fixing or attaching the second part to the guide wire inside a blood vessel of the person. In this manner, shorter guide wire/second part may be used, as one thereof needs not extend to the outside of the person.

Another alternative would be to introduce different fixators through different blood vessels (such as from arteries in the person's arms or legs), introduce a tubular element with multiple openings and multiple transport wires through one blood vessels and subsequently re-route transport wires and/or guide wires to enable snaring and subsequently be able to introduce additional tubular elements, if desired, through the openings though which the guide wires finally extend.

Having positioned the tubular element in the blood vessel (s), the fixator and the guide wire may be used for guiding further elements into the main tube, the branch tube, the main vessel and/or the branch vessel.

However, in some situations, the fixator may be in the way of such elements, especially when the branch vessel is not sufficiently long, such as if it divides into smaller vessels closely to the main vessel. In such situations, it may be desired to remove the fixator before introducing such further elements. Alternatively, the fixator may be collapsed and these other elements be introduced over the collapsed fixator. As such further elements are usually adapted to be guided over a standard guide wire, the fixator could be collapsible to obtain a final shape having an outer diameter corresponding to that of the guide wire. Thus, the guide wire could have a narrow portion adapted to receive the fixator when collapsed.

In such situations, among others, the step of providing the assembly may comprise providing an assembly in which the fixator may move independently of the guide wire, the assembly further comprising means preventing the fixator from travelling distally of the preventing means and/or beyond the end of the guide wire, the method further comprising the steps of, subsequent to the pulling step:

removing the fixator while maintaining the distal end of the guide wire inside the branch vessel, and introducing another element along the guide wire.

Thus, the still positioned guide wire (or the guide wire attached to the transport wire) may subsequently be used for introducing other elements into the branch vessel, such as filters, stents or grafts.

In fact, in a preferred embodiment, the introducing step comprises introducing another tubular element along the guide wire and positioning the other tubular element so as to extend from inside the tubular element (main tube and/or branch tube) and into the branch vessel.

This is especially useful when the positioning step comprises positioning the other tubular element so as to cover an area of the branch vessel where the fixator was fixed. In this manner, any vascular wall damage caused by the fixator may be covered by the other tubular element so as to avoid blood clotting which may be caused by such damages.

In a particular embodiment, the main blood vessel has a plurality of branch vessels and wherein:
the tubular element has:
a plurality of side openings,
a plurality of transport wires, the first part of all transport wires extending from the inner volume of the main tube and out of the tubular element through the end opening and the second part of each transport wire extending from the inner volume of the main tube and out of the tubular element through a separate side opening,
the providing step comprises providing a plurality of the assemblies,
the introducing step comprises introducing a fixator into each of the branch vessels (typically aortic branch vessels) and fixing the fixators in the branch vessels,
the fixing/attaching step comprises fixing/attaching each guide wire to a second part of a separate transport wire, where the branch vessel in which the guide wire is fixed corresponds to the second side through which the second part extends, and
the pulling step comprises pulling the first parts of the transport wires so as to have the guide wires extend from the individual fixators through the individual side openings and the main tube and toward, preferably to, the outside of the patient.

The position correspondence preferably is a position or angling in which a straight line from, such as perpendicularly to, the longitudinal axis or volume centre of the main tube may pass through a centre of the side opening or branch tube and enter the branch vessel, preferably at a central or longitudinal axis thereof.

Naturally, the plurality of transport wires may be replaced by a single element having a number of second parts extending as described but only a single part, for example, connected to all second parts, and extending as the first parts described.

It is clear that the tubular element may have a combination of one or more second openings and one or more branch tubes, where a side opening is an opening into a tube between the end portions thereof.

Typically, all side openings are provided in, or all branch tubes extend from, the main tube, and a fixator is used for each side opening/branch tube, but this is not a requirement. A branch tube may extend from another branch tube, which extends from (such as is fixed to or the like) the main tube. Also, a branch tube extending from the main tube may have a side opening therein. The positioning of the fixators will also make the positioning of this type of tubular element possible in the blood vessels of a person.

In that situation, the other branch tube—or the intermediate branch tube—may not need a fixator in the corresponding blood vessel, as the farther blood vessel into which the first branch tube is to be positioned (or toward which the first branch tube is to extend) may have a fixator, which may also be used for positioning, the intermediate branch tube.

In order for the fixator to fulfil its function as a fixator, it preferably can maintain attachment to the inner side of the blood vessel, when a pulling force of at least 0.1N is applied to the guide wire and the fixator.

The pulling of the guide wire may be intentional or non-intentional. Intentional pulling may be caused by re-direction of the guide wire or when directing additional elements into or toward the target blood vessel along the guide wire. Also, usually real-time imaging of the position of the fixator and other elements provided in the blood vessels of the person is performed, so that the identity or position of a fixator may be ascertained by pulling the proximal end or guide wire and identifying the fixator moving due to the pulling. Naturally, the fixator may move without detaching from the blood vessel. This detectable movement may be a slight sliding of the fixator within the blood vessel or simply the blood vessel moving as a result of the force exertion.

In the present context, the maintaining of the attachment is a movement of no more than than 1 mm of the fixator in relation to the blood vessel when the force is exerted in at least 10 seconds, such as at least 30 seconds, preferably at least 60 seconds. It is noted that no movement is desired, as any movement of the fixator while attached may cause damage to the blood vessel.

Depending on the type of surgical procedure and a number of other parameters, the fixator may be adapted to withstand a pulling force of more than 0.1N, such as 0.2N or more, preferably 0.3N or more, such as 0.4N or more, preferably 0.5N or more, such as 0.6N or more, preferably 0.7N or more, such as 0.8N or more, preferably 0.9N or more, such as 1N or more, preferably 1.5N or more, such as 2N or more, preferably 2.5N or more, such as 3N or more, preferably 3.5N or more, such as 4N or more, preferably 5N or more.

In the present context, the force which the fixator can withstand may be determined by testing the fixator in an animal blood vessel newly harvested from the animal and when immersed in saline. Blood vessels having diameters like those in human beings may be harvested from sheep, pigs, calves or cows. During the testing, the saline is not pumped through the vessel but kept more or less stand still. The force is exerted along a longitudinal axis of the blood vessel.

Clearly, a fixator will be adapted to be used in blood vessels of a given size or having a size within a specified diameter range. Thus, the testing should be performed under the same conditions, i.e. the fixator should be tested in a blood vessel having a size to which the fixator is prepared.

In a preferred embodiment, the fixator is designed to cover a minimum cross sectional area across the blood vessel to not to any substantial degree disturb the blood flow through the fixator in the blood vessel, thus securing e.g. arterial supply to the end-organ, for example the kidney or the intestine.

One manner of determining a cross sectional area of the fixator is to project the fixator onto a plane perpendicular to the longitudinal axis of the blood vessel. In this manner, a measure of the cross section may be obtained, such as a percentage of the inner cross section of the blood vessel, but if e.g. a basket-type fixator of the type seen in FIG. 1 is used, this cross section will not be that actually seen by the flowing blood. This basket-type fixator will have a fixing part engaging or attached to the blood vessel and which therefore is not relevant as to the cross section covered across the blood vessel cross section. However, this basket-type fixator may also have two end parts (proximal and distal parts) extending between the guide wire and the fixing part. These end parts will, in the projection, be overlapping and thus give an erroneous measure for the cross section seen by the blood. In this situation, the cross section of that end part having the largest cross section is a better measure for the cross section seen by the blood.

Preferably, the cross section(s) cover(s) less than 40%, such as less than 30%, preferably less than 20%, such as less than 10%, preferably less than 6% of the vessel cross section.

Naturally, the fixator may have a non-thrombogenic surface quality and flow promoting hydrodynamic design. Non-thrombogenic surfaces may be obtained by electro polishing the surfaces, for example.

In one embodiment, the fixator has:
- a deformable portion having a central portion adapted to attach to the inner side of the blood vessel at a predetermined length thereof, along a first longitudinal direction or axis of the blood vessel,
- a distal part attached to the deformable portion, and
- a proximal part attached to the deformable portion.

Preferably, the deformable portion is adapted to exert at least substantially the same force to the blood vessel along all of the predetermined length when the pulling force of at least 0.1N is exerted to the guide wire and fixator.

Preferably one or both of the distal and proximal parts is adapted to engage the guide wire and/or a stopping means fixed to the guide wire and ensuring that the fixator does not pass or move distally of the stopping means. In a preferred embodiment, both the distal and proximal parts define apertures through which the guide wire is adapted to slide. Even more preferably, the stopping means is then fixed to the guide wire and is not able to travel through the aperture of one or both of the distal and proximal ends.

Firstly, the central portion will usually be those parts of the fixator which extend or are adapted to extend the farthest from a central longitudinal axis of the fixator. Usually, the blood vessels are tubular with a circular cross section at least locally around the fixator, so that the central portion normally is a tubular portion positioned the farthest from the central axis. As will be described further below, this tubular portion need not have the same cross section along its entire length.

Preferably, the predetermined length is between 2 mm and 30 mm, such as between 3 mm and 20 mm, preferably between 5 and 20 mm, such as between 10 and 16 mm.

In one situation, the deformable portion forms a closed or unbroken surface adapted to engage, touch or attach to the blood vessel. In another situation, the deformable portion comprises openings or holes. The deformable portion of the latter situation may be more easily compressed and expanded and may be made of a weave or braided element. The openings or holes of the deformable portion may have a cross section of between 0.01 mm$^2$ and 10 mm$^2$, such as between 0.1 mm$^2$ and 1 mm$^2$. The larger the openings, the lower will the contact surface between the weave/braided element and the blood vessel wall, but the more easily may the weave/braided element be compacted for introduction into the blood vessel.

Naturally, a transition or intermediate part may be present between the central portion and the distal/proximal parts at which transition a slight force may be exerted to the blood vessel wall. Such parts are not relevant in relation to the preferred embodiment, where the primary focus is to ensure that no local parts exist where an excessive force is applied.

In this context, the exerting of at least the same force along the predetermined length may mean that, along this length, the force exerted at all positions along the length will be within 20% of a mean value of the force exerted along the length, such as within 10% of the mean value, preferably within 5% of the mean value.

In another situation, the "at least the same force" may mean that, along the length, no position exists at which a force exceeding a mean value of the force exerted along the length by more than 20%, such as 10%, preferably 5% of the mean value. Naturally, a lower force exertion is a much smaller problem than an excessive force exertion.

Usually, the force exerted at a point along the direction will be the same around the circumference of the central portion at a given position along the direction. Thus, the force may be summed or integrated around the circumference for the individual points. If the force deviates more than e.g. 10% around this circumference, individual angular positions around the direction may also be taken into account in order to identify or prevent such force "peaks".

In that or another embodiment, the fixator has:
- a deformable portion having a central portion adapted to attach to the inner side of the blood vessel,
- a distal part attached to the deformable portion,
- a proximal part attached to the deformable portion and being translatable, along a second longitudinal axis, in relation to the distal part, the distal part being positioned closer to the distal end of the guide wire than the proximal part, the central portion of the deformable portion circumscribing, in a plane perpendicular to the second longitudinal axis, a larger cross section when a first distance exists between the proximal and distal parts compared to a when a second distance exists between the proximal and distal parts, the second distance being larger than the first distance.

The discussion and function of the central/deformable portions and the distal/proximal parts may be as those described above.

The deformable portion circumscribes a cross section or a cross sectional area by the outermost parts of the deformable part defining this cross section or area. Naturally, the deformable part may comprise only a thin layer/weave or the like of material so that the overall cross section of the deformable portion is a narrow, closed curve, but it may also have an internal structure in order to keep the deformable portion expanded so as to attach to the blood vessel. One general, preferred type of deformable portion is a pre-shaped element automatically expanding when in the vessel. In this situation, no inner structure may be required to obtain the expansion.

In this context, the second longitudinal axis preferably may be an axis around which the deformable portion or the central portion is symmetric. Also, it may be desired that the proximal and distal parts define apertures at the second longitudinal axis, so that the guide wire may extend through the proximal and distal parts along the second longitudinal axis. Usually, the first and second axes will be parallel or at least substantially parallel when the fixator is positioned in the blood vessel.

When forcing the distal and proximal parts toward each other from the second to the first position, the cross section circumscribed by the deformable portion increases. This cross section may be the cross section at one position along (in a plane perpendicular to) the longitudinal axis or may be a mean cross section along the longitudinal axis over the length or extent of the deformable portion or central portion.

Usually, when positioned in the blood vessel, the expansion of the deformable portion is limited by the blood vessel. Outside the blood vessel, the expansion usually can take place for the deformable portion to reach cross sections larger than that of the blood vessel diameter or type for which the deformable portion or fixator is intended.

In a preferred embodiment, the preventing means prevent the distal part from travelling beyond the distal end. In this respect, the proximal part preferably is movable in relation to the distal part, the central portion and the guide wire, so that the pulling force is exerted to the distal part, which may, in the above fixator, cause the deformable portion to attempt to obtain a larger cross section and thus engage the blood vessel with a higher gripping force. The reason for this is that the attachment of the deformable portion to the blood vessel will act to have the pulling force actually force the distal part toward the proximal part which is more fixed in relation to the blood vessel. Thus, as the grip or engagement increases when the guide wire is pulled, the force with which the deformable portion engages the blood vessel, when no or only little force is exerted, may be low or weak, which causes less damage to the vessel walls.

However, due to the fact that the pulling force in this situation acts between the distal part and the central portion, the central portion will typically react by trying to increase the cross sectional area the most at the most distal parts. This increase is counteracted by the blood vessel wall, whereby a larger force is exerted thereto. This may not be desired, and different manners exist of counteracting this effect.

In one situation, the central portion has a rest shape that:
  circumscribes a first cross sectional area in a plane perpendicular to the second longitudinal axis and at a first position along the second longitudinal axis and
  circumscribes a second cross sectional area in a plane perpendicular to the second longitudinal axis and at a second position along the second longitudinal axis,
wherein the second position is closer to the distal part than the first position, the second cross sectional area being smaller than the first cross sectional area.

In this context, a rest shape is the shape which the central portion has when no forces act on it (except possibly gravity), including forces acting to force the distal and proximal parts toward each other, such as when the central portion is positioned on a table or horizontal surface.

Also, in this context, the first cross sectional area is at least 2%, such as at least 5%, preferably at least 7%, such as at least 10%, preferably as at least 15%, such as at least 20%, preferably at least 40%, such as at least 60% larger than the second cross sectional area.

When this fixator is positioned in the blood vessel, the central portion may or may not attach to the inner surface of the blood vessel at the second position with the smaller cross sectional area, when no or a small pulling force is exerted. However, when a pulling force is applied to the guide wire, the lower cross sectional area at the second position preferably acts to increase in size and/or have a more even force exerted to the blood vessel along the length or area of the deformable portion or the central portion. As described above, the pulling of the distal part primarily acts to increase the cross sectional area at positions closer to the distal end.

Preferably, the second position is a position within or at a distance of at the most 80%, such as at the most 60%, preferably at the most 40%, such as at the most 25%, preferably at the most 10%, such as at the most 5%, preferably at the most 2% of an extent of the central portion or the deformable portion along the second axis, from the distal end of the central portion.

In another situation, the central portion is adapted to, when the proximal and distal parts are forced toward each other along the second longitudinal axis:
  circumscribe a third cross sectional area in a plane perpendicular to the second longitudinal axis and at a third position along the second longitudinal axis, and,
  circumscribe a fourth cross sectional area in a plane perpendicular to the second longitudinal axis and at a fourth position along the second longitudinal axis,
wherein the third position is closer to the distal part than the fourth position, the third cross sectional area being smaller than the fourth cross sectional area.

As mentioned above, the cross sections of the deformable portion or central portion will be limited by the blood vessel. Thus, this situation is normally seen when the fixator is outside the vessel and not limited in that manner.

When the proximal and distal parts are forced toward each other with the above-mentioned at least 0.1N, such as 0.2N, preferably 0.3N, such, as 0.4N, preferably 0.5N, such as 0.6N, preferably 0.7N, such as 0.8N, preferably 0.9N, such as 1N, preferably 1.5N, such as 2N, preferably 2.5N, such as 3N, preferably 3.5N, such as 4N, preferably 5N, it will expand (obtain a larger cross sectional area) more at the fourth position and thus not at the distal part. As indicated above, preferably, the third position is a position within or a distance of at the most 80%, such as at the most 60%, preferably at the most 40%, such as at the most 25%, preferably at the most 10%, such as at the most 5%, preferably at the most 2% of an extent of the central portion or the deformable portion along the second axis, from the distal end of the central portion.

In general, the deformable portion may comprise a wire mesh or braided wires. The wire density of the deformable portion preferably is between 0.1 and 15 wires per mm, such as between 0.2 and 5 wires per mm, preferably between 0.5 and 3 wires/mm along the longitudinal direction. Also, the wire thickness may be between 0.01 mm and 1 mm, between 0.05 mm and 0.5 mm, preferably between 0.07 mm and 0.2 mm.

In a preferred embodiment, 40 wires (0.1 mm diameter) are used in a braid having a maximum diameter of 7 mm over a length of 14 mm when expanded and which, in the non-expanded shape, has a length of 40 mm.

In one situation, the wire mesh/braid has a wire density of the wire mesh/braid being higher at one of the second position, the third position, and a distal end of the central portion, than at one of the first position, the fourth position, and a proximal end, of the central portion. In this situation, the higher wire density (number of wires per distance unit along the second axis) will make the expansion (increase in cross sectional area) lower than where the wire density is lower; the higher wire density makes the pertaining parts of the deformable portion more stiff.

An alternative to or in addition to the wire density difference, the deformable portion may comprise a wire mesh/braid, wherein a wire thickness of the wire mesh/braid is higher at one of a the second position, the third position, and a distal end of the central portion, than at one of the first position, the fourth position, and a proximal end of the central portion. This wire thickness increase will also make the pertaining part stiffer.

A further alternative or addition is one comprising a circumference limiting element at one of the second position, the third position, and a distal end of the central portion. In this manner, the circumference and thus cross sectional area at the third position may be limited so as to exert only a predetermined force to the blood vessel. Any pulling of the guide wire will thus direct the force to other parts of the deformable portion further toward the proximal portion.

In the following, preferred embodiments of the invention will be described with reference to the drawing, wherein

BRIEF DESCRIPTION OF THE DRAWINGS

FIG. 1 is a schematic illustration of a fixator according to a first embodiment of the invention, when disconnected from a retrieving catheter and with a delivery catheter retracted from the fixing part;

FIGS. 2 and 3 are schematic illustrations of the fixator in FIG. 1 in different situations of use;

FIG. 5 is an exploded view of the fixator in FIG. 4;

FIG. 6 illustrates a third embodiment of a fixator according to the invention;

DETAILED DESCRIPTION OF EMBODIMENTS OF THE INVENTION

Figure 3:
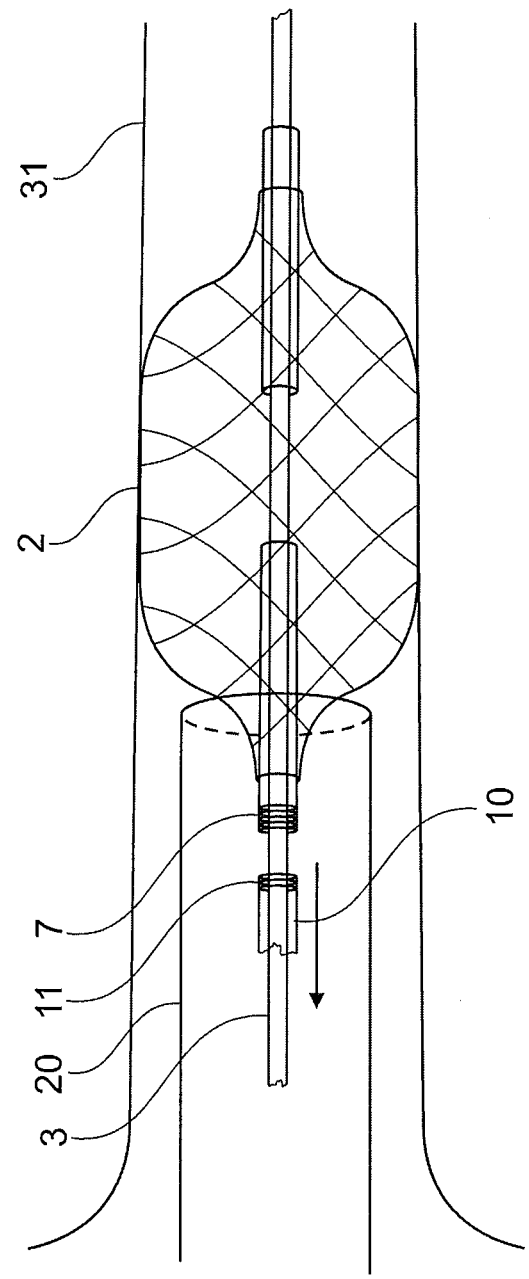

In the following description the terms "distal" and "proximal" are used to denote the mutual location of two corresponding parts, wherein the heart is used as reference, such that anatomical structures that are closer to the heart are denoted as proximal and details that are farther from the heart are denoted as distal. For parts of a medical device, such as the present fixator, the definition is instead based on the surgeon as reference. Hence, details that are closer to the surgeon are denoted as proximal and details that are farther from the surgeon are denoted as distal.

In FIG. 1, a first embodiment of a fixator 1 in accordance with the invention is shown. The fixator involves a flow transparent retainer or fixing part 2, which in the shown embodiment consists of a metal frame basket. The fixing part 2 is arranged on a guide wire 3. In FIG. 1, a distal tubular sleeve 5 is arranged at the distal end 2a of the fixing part. The distal sleeve 5 is fixed (releasably or not) to the guide wire 3, or at least prevented from leaving the guide wire, whereas the proximal end 2b of the fixing part 2 is arranged to slide over the guide wire 3 by means of a proximal tubular sleeve 4. The proximal and distal sleeves 4 and 5 jointly limit the possible deformation of the fixing part 2 as its ends 2a and 2b are forced toward each other, which will be described below. The distal end 2a of the fixator 1 comprises a distal end part 6, which may be a continuation of the guide wire 3, and which is soft and pliable in order not to cause damage in the target vessel. Guide wires for catheterisation are typically of the dimensions between 0.14 and 0.89 mm in circumference. These are very pliable and atraumatic with a hydrophilic slippery surface that allows catheterisation of small, stenotic and kinked arteries, without damage to the target vessel wall.

The proximal end 2b of the fixing part 2 involves a connecting member 7 for connecting the fixing part 2 to a retrieving catheter 10. In the shown first embodiment, the connecting member 7 has internal threads that are arranged on the inside of the proximal tubular sleeve 4. The retrieving catheter 10, on the other hand, comprises a corresponding connecting member 11 in the form of external threads for mutual connection of the retrieving catheter 10 and the fixing part 2.

In general (see FIG. 10), the fixing part or deformable portion 2 has a central portion C, which attaches to or engages the vessel when deployed, and which is connected to the sleeves 4/5 via the end portions 2a and 2b.

Preferably, the fixator 1 also has or is supplied with or inside a delivery catheter 20 in the form of a hose of a diameter adapted to house the fixing part 2 and the retrieving catheter 10. The delivery catheter 20 enables the positioning of the fixing part 2 as it allows the fixing part to be fully housed therein during the introduction and positioning of the fixator 1. It would however also be possible to keep the fixing part collapsed without housing it inside a delivery catheter 20, e.g. by keeping the sleeves separated from each other by means of e.g. a screw controlled arrangement.

The length of the guide wire 3, the retrieving catheter 10 and the delivery catheter 20 must be sufficient to allow their respective proximal ends to be accessible to and manoeuvrable by the surgeon when the corresponding distal ends are located in a target vessel. Typically, the guide wire 3, the retrieving catheter 10 and the delivery catheter 20 all have lengths between 0.5 and 2.8 meters.

The function of the fixator will be described step by step in an exemplary mode of use and with reference to FIGS. 2-4. A further description is found in relation to FIGS. 13-16.

In a first step, as shown in FIG. 2, the delivery catheter 20 is inserted into a target vessel 30, defined by a vessel wall 31 and an opening 32 into e.g. the aorta. During the insertion of the fixator 1, only the pliable distal end part 6 of the fixator 1 extends outside of the delivery catheter 20. The fixing part 2 is undeployed or collapsed in the radial direction such that it fits inside the delivery catheter 20. In order to allow for the radial collapse, the fixing part 2 is extended in the axial direction with the distal sleeve 5 at a relatively large distance from the proximal sleeve 4. During the insertion, the connecting member 7 of the fixing part 2 is connected to the connecting member 11 of the retrieving catheter 10. The insertion of a catheter into an unblocked vessel is in itself conventional and is therefore not described in detail in this application.

In a second step, when the delivery catheter 20 is located inside the target vessel 30, the fixing part 2 is pushed out from the inside of the delivery catheter 20. The pushing of the fixing part 2 is achieved by means of mutual movement of the delivery catheter 20 on the one hand, and the retrieving catheter 10 on the other hand. As the fixing part 2 exits the delivery catheter 20 it strives to regain its original shape, which is individually adapted to the diameter of the vessel 30 such that it exerts a certain pressure on the vessel wall 31. This pressure should be as low as possible in order not to harm the vessel, but it must however be sufficient to keep the fixator from moving with respect to the vessel. The fixing part 2 has a flow transparent form that allows nutritive blood flow through it. In the present embodiment, the fixing part 2 comprises crosswise woven threads, which are adapted to expand to a diameter that is slightly larger than an inside diameter of the relevant blood vessel so as to exert a pressure on the blood vessel wall that restrains the fixing part 2 from moving with respect to the target blood vessel 30. The blood flow is allowed to flow through the crosswise woven threads.

Even though it is possible to provide the fixing part 2 with means for obtaining the expanded shape, it is preferred that the fixing part, and here the crosswise woven threads, has an expanded rest shape, so that the expansion merely is a movement toward the rest shape. This type of fixing part may be obtained by providing the threads in the desired, expanded shape and heat treating the threads to have or give this expanded shape the rest shape.

A third step, where the fixing part 2 is fully deployed outside the delivery catheter 20 and at location inside the target vessel, is illustrated in FIG. 3. In this third step, the retrieving catheter 10 is disconnected from the fixing part 2. In the present embodiment, this disconnecting is achieved in that the retrieving catheter 10 is rotated with respect to the fixing part 2, which is restricted from rotating due to its contact with the vessel wall 31, such that the connecting member 11 of the retrieving catheter 10 is unscrewed from the connecting member 7 of the fixing part 2.

In a fourth step, when the retrieving catheter 10 has been disconnected from the fixing part 2, both the retrieving catheter 10 and the delivery catheter 20 may be withdrawn from the target vessel and leaving only the fixing part 2 and the guide wire 3 in the vessel 30. The fixing part 2 is arranged to not hinder the blood flow through the vessel.

In order to ensure that the fixing part 2 is not disconnected from the guide wire 3 when the guide wire 3 is pulled, the proximal sleeve 4 and/or the distal sleeve 5 is releasably fixed to the guide wire 3, such as via a threaded connection, a snap fit or the like.

Figure 4:
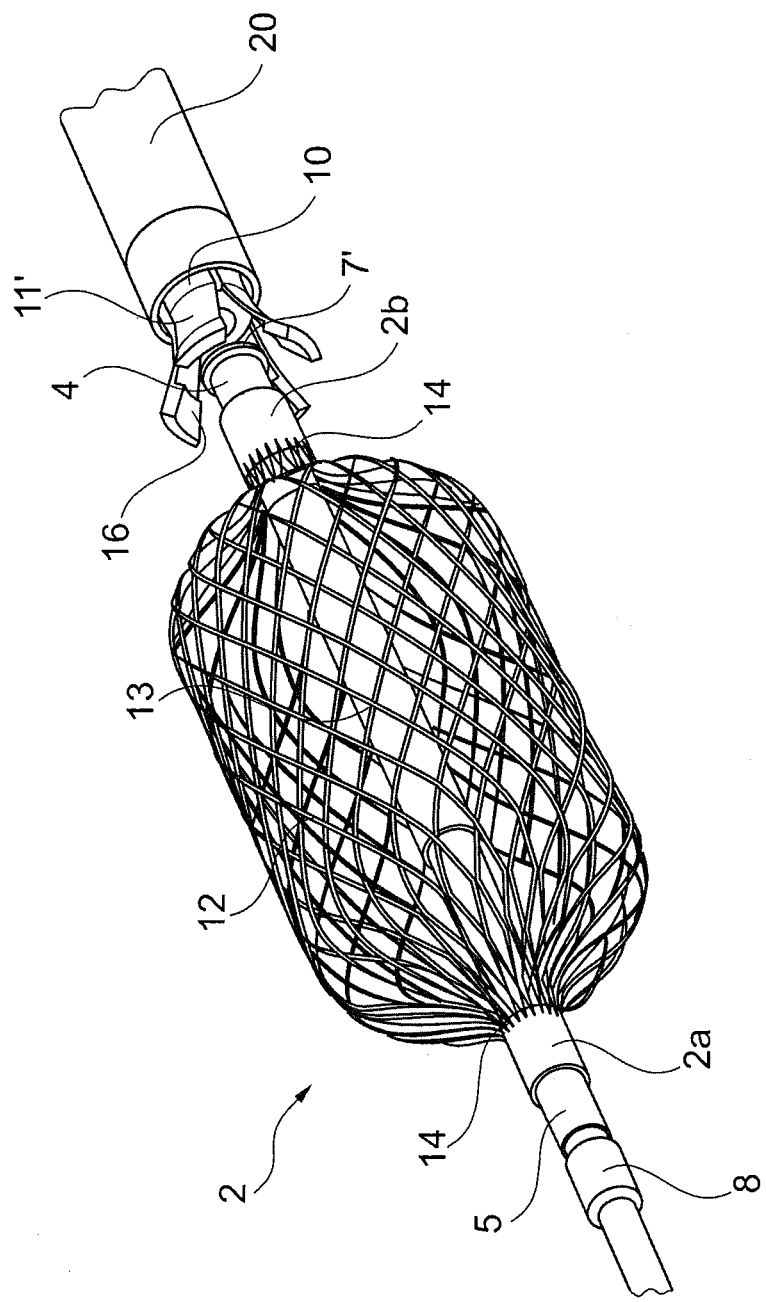
FIG. 4 illustrates a second embodiment of a fixator according to the invention.

FIG. 4 illustrates a second embodiment of a fixator according to the invention.

Naturally, details corresponding to details of the first embodiment are denoted with the same reference numerals, whereas details that are different from details of the first embodiment but that have the same function are denoted with the same reference numerals with an added apostrophe. A number of differences exist both in construction and use of the first and second embodiments. It is clear that such features, may be interchanged between the embodiments if desired.

In the second embodiment of the fixator 1, the threaded attachment between the proximal sleeve 4 and the retrieving catheter 10 of FIG. 1 is replaced by a snap-on lock, including a connecting member 11' on the retrieving catheter 10 in the form of a claw like grasping unit with claws or projections 16 and a corresponding connecting member 7' in the form of a ring shaped stopper on, or in connection to, the proximal sleeve 4. The shape of the projections 16 is adapted to interlock with the ring shaped stopper as the connecting member 11' is retracted into the delivery catheter 20, and as the delivery catheter 20 is pushed over the connecting member 11'. Thus, the delivery catheter forces the projections to grasp over the connecting member when the fixator is retracted towards the retrieval catheter by the guide wire.

In FIG. 4, individual threads/wires 12 of the basket shaped fixing part 2 are clearly visible. The threads/wires 12 may be welded together at crossing points 13, or they may be braided such that they pass each other by turns over and under each other. The ends 14 of the threads are securely fastened to the sleeves 4 and 5, respectively, either by welding, gluing or sewing or in any other suitable manner. Further, in FIG. 4, the connecting member 7' in the form of the ring shaped stopper may be seen inside the claw like grasping unit that constitutes the connecting member 11' on the retrieving catheter 10.

In the second embodiment, both sleeves 4 and 5 are arranged to slide over the guide wire 3. However, a stopper 8 positioned on the guide wire 3 prevents the sleeves from moving over the distal end of the guide wire 3 and thus disconnect fully from the guide wire 3.

Alternatively, the distal sleeve 5 may be detachably fixed, using e.g. any of the fastening methods between catheter 10 and sleeve 4. The reason for this detachability or slidability will be described further below.

Further, from this view it is apparent that the function of the sleeves is somewhat different in this embodiment with respect to their function in the first embodiment. In this embodiment, the connecting member 7' is arranged directly on the proximal sleeve 4 of the fixing part. The proximal sleeve 4 is partly and fixedly housed inside a protective sleeve 15 (see also FIG. 5), which extends inside the basket shaped fixing part 2 and also partly houses the distal sleeve 5. When the fixing part 2 is in its deployed shape, there is a gap between the distal and the proximal sleeves 5 and 4, respectively. As the guide wire 3 is pulled, or the fixing part 2 is allowed to expand toward its rest shape, the fixing part 2 is fixed to the vessel wall, and any pulling force applied to the distal sleeve 5 will thus act to compress the fixing part in the axial direction. Thus, the sleeves move closer to each other, until the proximal end 5b of the distal sleeve 5 reaches the distal end 4a of the proximal sleeve 4. The contact between these ends of the sleeves thus limits the axial deformation of the fixing part 2. The distal end 5a of the distal sleeve 5 is arranged to interact with the stopper 8 on the guide wire 3 and limit the axial movement of the guide wire 3 with respect to the fixing part 2, as described above.

In a third embodiment the guide wire 3' is a hypotube, as is shown in FIG. 6. The hypotube may be made of Nitinol or stainless steel and is preferably coated by a hydrophilic coating, such as e.g. PTFE, in order to create a slippery contact surface to the retrieving catheter 10. The hypotube may be just as flexible as a guide wire, or more flexible. The suitable size of a hypotube may range from 0.5 mm to about 2 mm with a wall thickness of about 0.04 to 0.2 mm.

Preferably, the hypotube should have a sufficiently large inner diameter to successfully house a stiff conveying wire 25. The stiff conveying wire 25 is helpful for guiding the insertion of the fixator 1. In order for the guide wire 3' to be rerouted, it has to be flexible and pliable.

However, due to the pliability of the guide wire 3', it may be difficult to control the guide wire 3' and to guide it into the target blood vessel. Hence, the stiff conveying wire 25 will make it possible to control the guide wire 3' during insertion. The conveying wire 25 enables the insertion of further catheters and or stent branches over the guide wire. With a stiff conveying wire inside the guide wire 3', the stent graft branch can be introduced over the (hypo-)tubular guide wire 3' housing a conveying wire.

The stiff conveying wire 25 may be withdrawn from inside the guide wire 3' when the fixing part 2 has been located in the target vessel 30. When the stiff conveying wire 25 has been withdrawn from inside the guide wire 3', the guide, wire is sufficiently pliable and flexible to be rerouted inside an arterial system in an atraumatic manner.

The guide wire 3' may be provided with an opening 26 near its distal end. With such an opening 26 the guide wire 3' may constitute a conduit for locally distributing a pharmaceutical via said opening 26. In many situations, e.g. when treating tumours, it is of interest to deliver a pharmaceutical agent locally, especially since certain pharmaceuticals, although effectively treating a disease process at one location, may be harmful if distributed systematically. Until now there has been no reliable way of delivering a pharmaceutical endovascularly over a period of time.

By means of a guide wire 3' in the form of a hypotube comprising a fixing part 2 it is possible to fix the end of the hypotube inside a target vessel, and to deliver a desired amount of a pharmaceutical through the opening 26 at the desired location, without risking that the hypotube will move and lose this location.

Naturally, the fixator of FIG. 6 may, for most parts, be similar to the fixator according the first and second embodiments. For example, a stopper 8 may be provided on the guide wire 3' for interaction with the distal sleeve 5, and a protective sleeve 15, which extends inside the basket shaped fixing part 2, is arranged to partly house the distal sleeve 5. Further, the distal end 6 of the guide wire 3' is preferably soft and pliable in order not to cause damage inside the body. Also, the proximal part of the guide wire 3', e.g. proximal to the fixing part 2, is also pliable in order to allow rerouting. In a conventional manner, the tip of the guide wire 3', may include a 180° bend (not shown) that prevents arterial damage in the target vessel.

Figure 7:
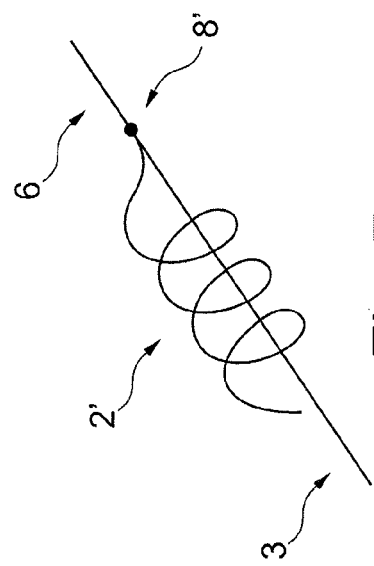
FIG. 7 illustrates a fourth embodiment of a fixator according to the invention.

FIG. 7 illustrates a fourth embodiment of a fixing, part 2' for use in a fixator according to the invention. This fixing part 2' has the shape of a helical spring and is still releasably fixed to the guide wire 3 with a stopper 8'. The distal end of the fixing part 2' may have a ring-shaped element through which the guide wire 3 extends and which engages with the stopper 8' to prevent the fixing part 2' from moving over the distal end of the guide wire 3. This fixing part 2' has the advantage of being extremely simple in manufacture as well as presenting very little flow resistance in the blood vessel.

Introduction and retraction of the fixing part 2' may be performed using a catheter. Withdrawing the pre-formed fixing part 2' will simply rotate this without scraping or damaging the vessel wall.

In the present embodiments the fixing part 2/2' preferably comprises a metal structure of weaved, coiled and/or braided wires or threads, preferably from Nitinol. Other biocompatible materials with similar properties may also be used, e.g. other alloys or plastics. The material must be sufficiently flexible to allow it to be collapsed without being plastically deformed, but at the same time sufficiently rigid to exert a pressure when released inside a vessel. In a specific method of producing the fixing part 2/2', a Laser cut length of a braided Nitinol tube is drawn around a template of a desired shape. The ends of the Nitinol tube are shrunk around the ends of the template and a heat treatment is performed in this position, such that the Nitinol basket, i.e. the fixator, adapts to this new shape. The fixator will then strive to regain this shape whenever unaffected by exterior forces.

Alternative fixing parts 2/2' may have a larger general contact area with the blood vessel, such as when using a piece of cloth, material or the like, which is supported on the coiled spring or the braided wire so as to better even out or enlarge the actual contact surface between the fixing part and the blood vessel wall.

As will be described in more detail below, the advantageous arrangement of the above embodiments enables the fixing part to remain in place as the guide wire 3 is subject to tension, e.g. from rerouting of its proximal end. The proximal sleeve 4 is arranged to slide on the guide wire 3 such that it remains unaffected by it, whereas the distal sleeve 5 is prevented from travelling toward the distal end of the guide wire 3. Due to this arrangement any pulling forces on the guide wire 3 will compress the fixing part 2 in the axial direction, due to the friction between the vessel wall 31 and the proximal part of the fixing part 2, such that the fixing part 2 is expanded in the radial direction, see FIG. 8. Hence, the pressure against the vessel wall 31 will increase as a function of the pulling force on the guide wire, such that the increased friction force between the fixing part 2 and the vessel wall 31 instantaneously increases with the increased pulling force. Therefore, by means of the increased friction force, the fixing part 2 is kept in place.

This arrangement allows for the fixing part to exert only a minimum force on the vessel wall 31 as long as it is unaffected by any pulling force, in order to minimise the traumatic effect on said vessel. Also, during most parts of a normal operational procedure, the guide wire is not affected by any forces at all. The function of the fixator 1 is mainly to retain the position inside the target vessel. Pulling forces normally only arise when the guide wire 3 is being rerouted. The axial compression of the fixing part may be limited by interaction of the sleeves 4 and 5, as they come into contact with each other in response to a pulling force on the guide wire 3. Hence, the maximum radial extension of the fixing part 2, and thus the maximal radial force exerted by it on the vessel wall, can be limited by the available distance between the sleeves; the greater the distance, the greater the possible axial compression and consequent radial extension.

Figure 8:
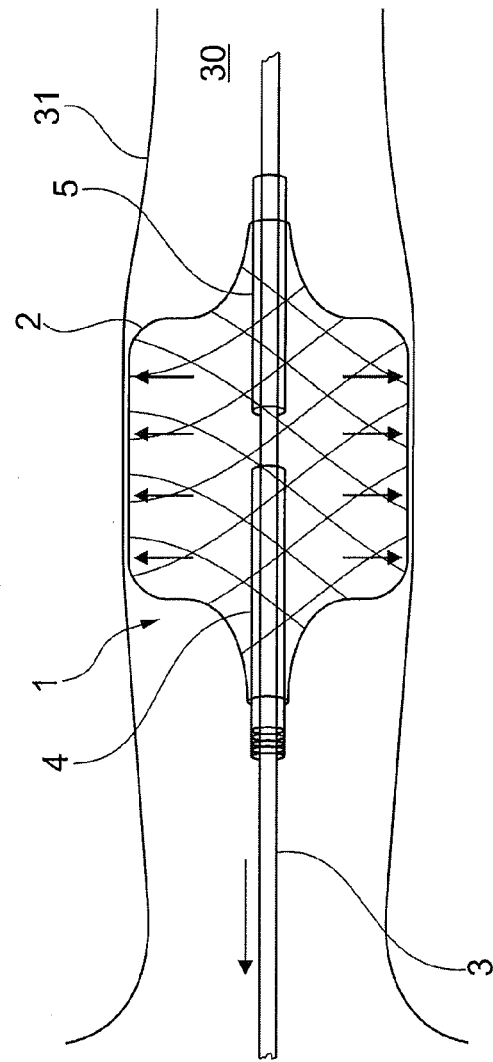
FIG. 8 illustrates the force exertion during attachment to the blood vessel.
Figure 9:
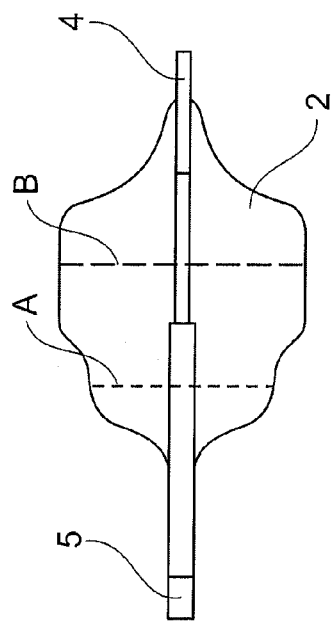
FIG. 9 illustrates the force exertion outside the blood vessel.

It has been found, however, that even though, as is seen in FIG. 8, the fixing part 2 is bounded perpendicular to its longitudinal axis, of the dimensions (primarily thickness or radius) of the blood vessel 30, there may be a difference along the longitudinal direction of the force exerted to the blood vessel. The cause is that as the fixing part or deformable portion 2 engages the vessel wall 31 and the distal sleeve pulled, the force is not distributed evenly over the area engaged by the fixing part 2 but mainly at the distal part thereof. In FIG. 9, the shape of a fixing part 2 in an element more flexible than a blood vessel is illustrated. It is seen that the cross sectional area (or radius if circular or having rotation symmetry) at the longitudinal position A is larger than at position B which is positioned more proximal than A.

Figure 10:
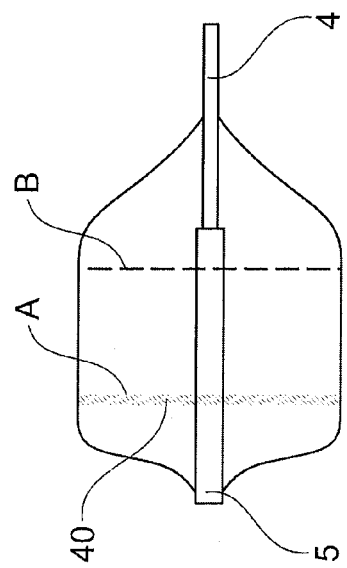
FIGS. 10-12 illustrate different embodiments of a deformable portion for the present fixator.
Figure 11:
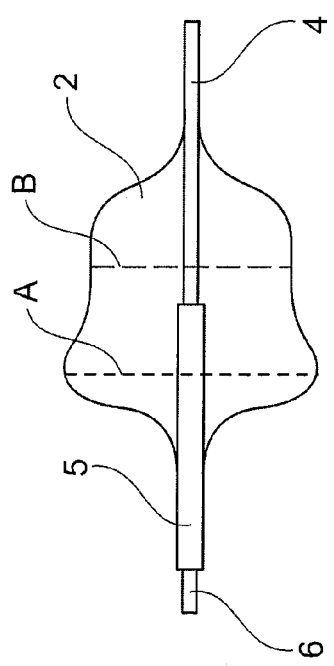
Figure 12:
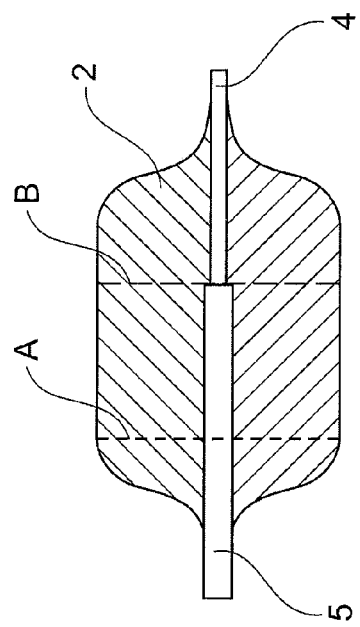

Thus, in order to distribute this force more evenly, different solutions are illustrated in FIGS. 10-12.

In FIG. 10, the fixing part 2 has an asymmetric shape, when non-stressed and/or in a non-compressed state, over the longitudinal length which is to engage the blood vessel, where a part of the fixing part 2 closer to the distal end or sleeve 5 has a smaller cross sectional area (or radius if circular or having rotation symmetry) at position A than closer to the proximal sleeve 4, such as at position B.

Thus, when positioned in the blood vessel 30 and without pulling the guide wire 3, the shape of the fixing part 2 of FIG. 10 may look like in FIG. 8, where the force exerted to the wall 31 is uneven but still quite low. When the guide wire 3 is pulled, however, the increased force exerted on the wall 31 may be more even, as the more narrow rest shape of the distal part (around position A) of the fixing part 2 will act to counteract a large expansion and thus force increase at that part.

In FIG. 11, the rest shape or non-stressed/non-compressed shape of the fixing part 2 may be symmetric but the expandability of the fixing part 2 asymmetric along the longitudinal direction. In FIG. 11, the fixing part 2 is provided as a wire mesh with a higher wire density at position A compared to position B. Thus, when compressing the fixing part 2 outside the blood vessel 30, an asymmetric shape as that illustrated in FIG. 10 may be obtained. Also, when compressing the fixing part 2 or pulling the guide wire 3 when the fixing part 2 is deployed in the vessel 30, the higher wire density at position A will act to even out the pressure exerted and ensure that more force is applied around position B.

Naturally, the same functionality may be obtained by adapting the wire thickness or other parameters of the wire mesh.

In FIG. 12, another manner is illustrated which prevents excessive force exerting on the vessel 30 close to the distal end of the fixing part 2. In this embodiment, a circumference limiting element 40 is provided at the distal end at position A. This element 40 prevents the circumference of the fixing part 2 from exceeding a predetermined length, whereby any further deformation will be required at the more proximal parts, such as around position B. This circumference limiting element 40 may be a non-stretchable element, such as a band, a wire or the like.

In general, it is noted that different types of materials for the fixing part 2 and different constellations thereof may be chosen. The overall functionality is that the fixing part 2 should be able to engage the vessel wall while allowing a blood flow there through.

The overall advantages of using the present fixator 1 is now described with reference to FIGS. 13-16. This description of a use of the fixator is limited to the positioning of a branched stent graft in a person to treat aortic aneurysms with aneurysm extension in the thoraco-abdominal aorta. It is noted that many other reasons exist for wishing to catheterize blood vessels of small dimensions such as the renal arteries to the kidneys, the visceral arteries to the intestines or the arteries supplying the liver, etc. Accessing these arteries and maintaining a catheterization of these arteries is difficult especially when concomitant catheterisation of several arteries is taking place simultaneously.

Figure 13:
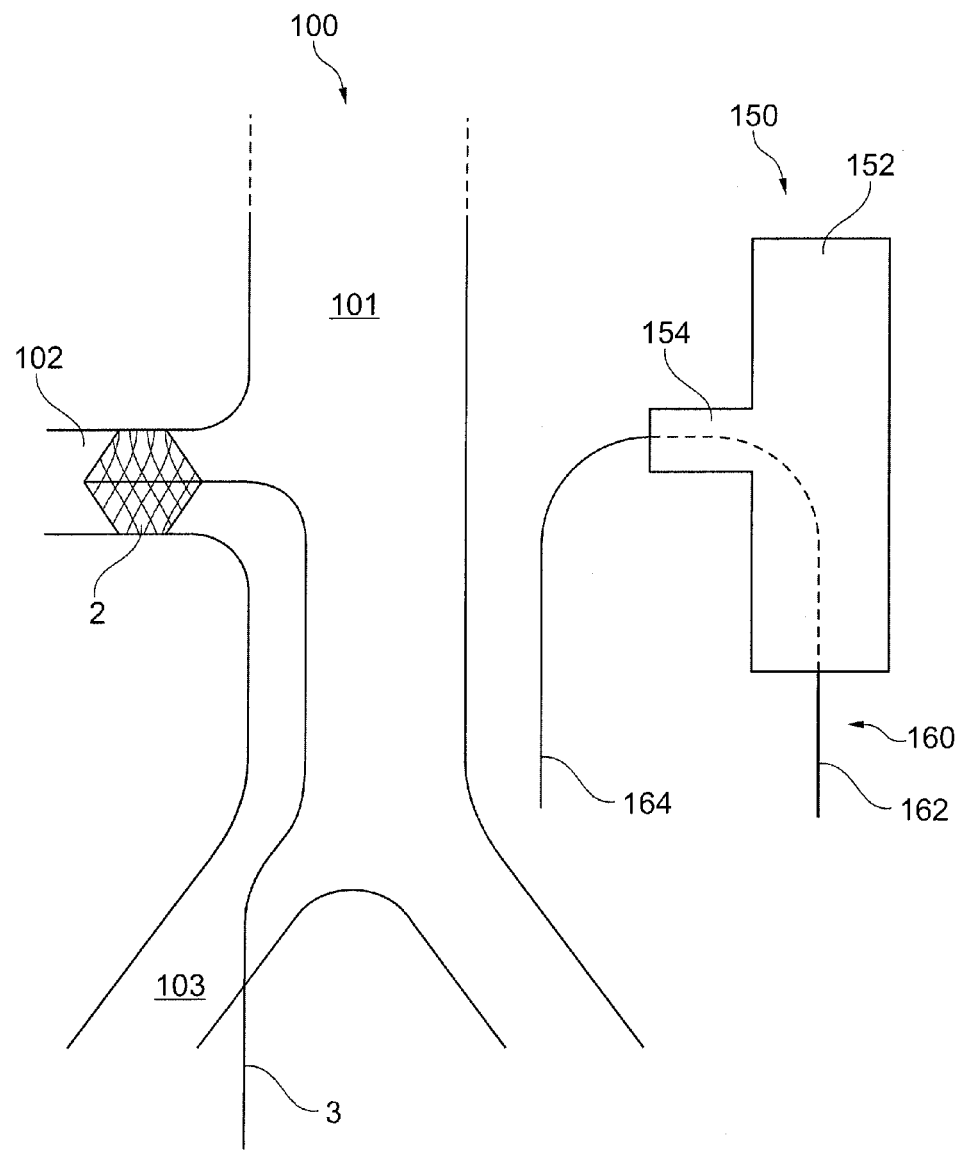
FIGS. 13-16 illustrate a surgical procedure using the present fixator for positioning a branched stent graft in the aorta of a person.

FIG. 13 illustrates the human artery system with the aorta 101 from which a renal artery 102 feeds a kidney and an artery 103 leads toward a leg. As is usual in many of these procedures, the aorta 101 is accessed via the common iliac artery 103 via an arterial puncture. Then, a fixator with a fixing part 2 and a guide wire 3 is positioned as indicated above. The guide wire 3 extends out of the arterial puncture.

It is the goal of the procedure to position the graft 150 inside the system 100 with the main lumen 152 of the graft 150 in the aorta 101 and the branch 154 toward and into the artery 102. The graft 150 has a vertical longitudinal axis, openings at the upper and lower ends as well as a side opening in the branch 154. In the graft 150, a transport wire 162 is positioned which stretches through the main lumen 152 and the branch 154 with ends 164 and 162, respectively.

Figure 14:
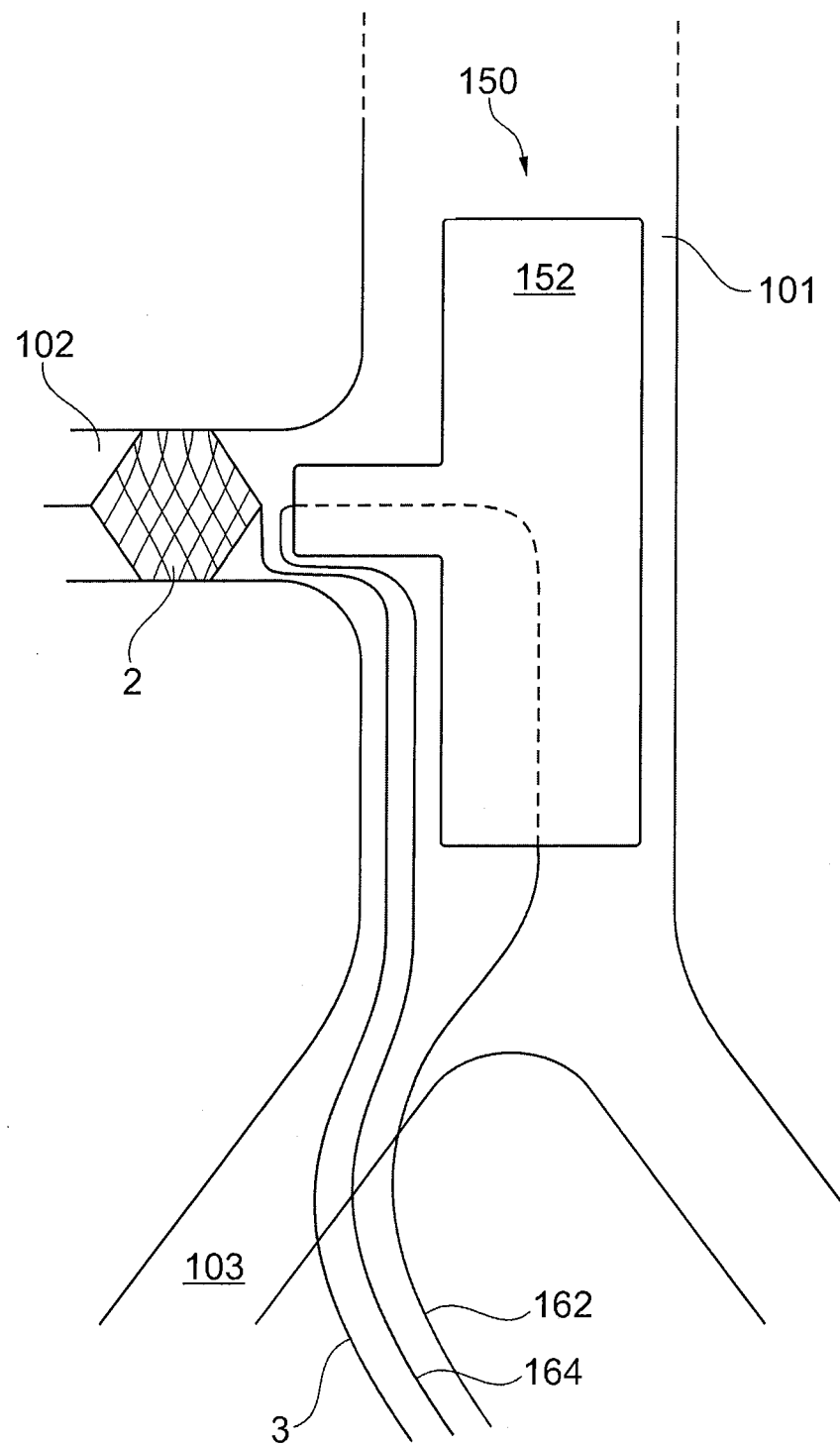
Figure 15:
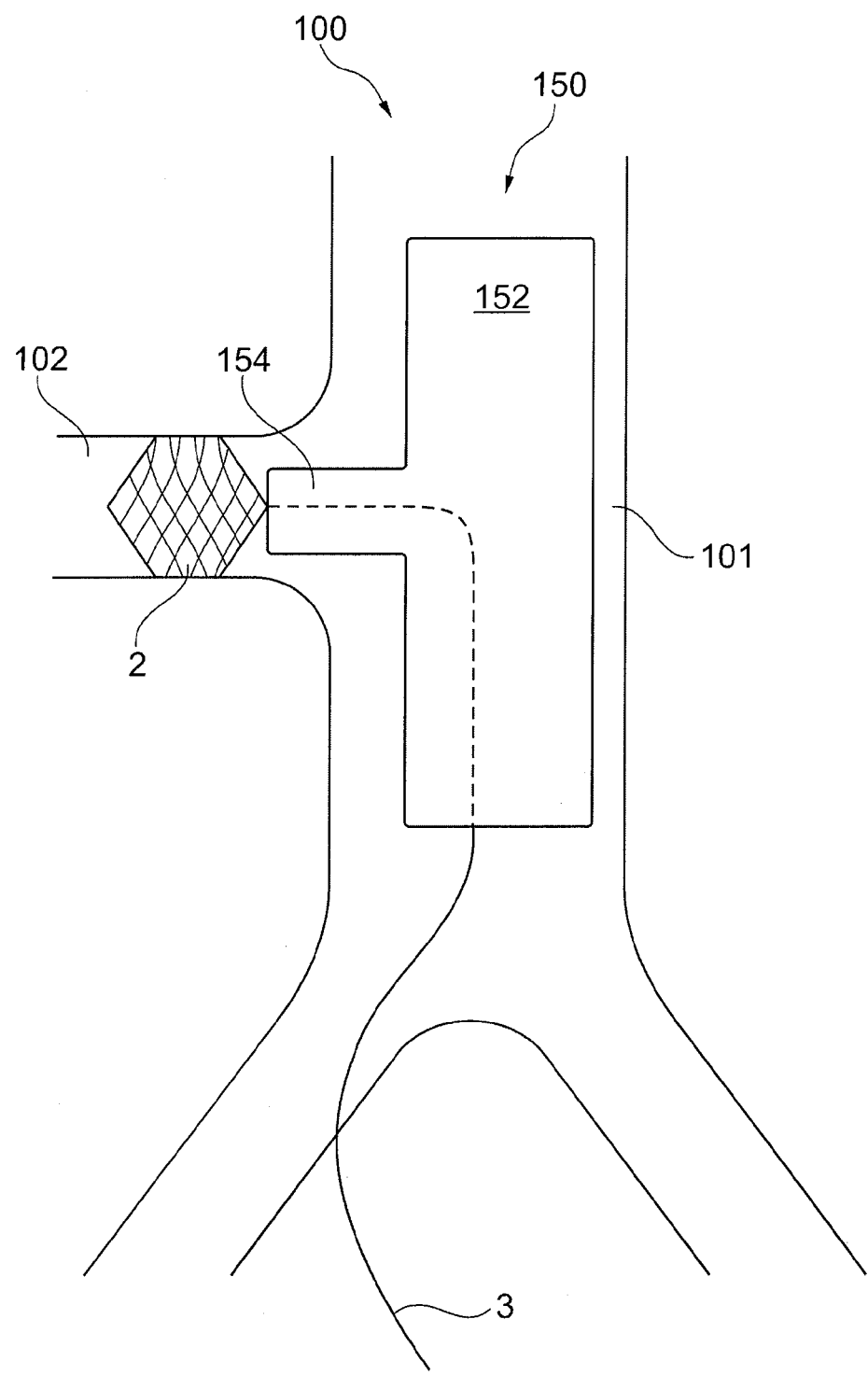

In FIG. 14, the graft 150 has been positioned in the aorta 101. Conventionally, the graft 150 may be compressed, positioned within a delivery introducer and positioned in the aorta 101.

The graft 150 is introduced through the same artery puncture, and the ends 162 and 164 extend outside the person together with the guide wire 3. In this manner, the subsequent fixing/snaring is facilitated, as this may be performed outside the body of the person.

Having positioned the graft 150 in the aorta 101, it is partly deployed in order to make the transport wire movable within the graft 150.

Subsequently, the guide wire 3 and the end 164 are attached to each other, and the end 162 pulled, so that the guide wire 3 and end 164 are re-introduced into the system 100 and through the branch 154, the main lumen 152 and out through the artery puncture so that (see FIG. 15) the guide wire 3 now extends from the fixing part 2 through the branch 154, the main lumen 152 and out of the patient. This procedure or re-positioning of the guide wire 3 will require some pulling of the fixing part 2, whereby its capability in this respect is used.

Having now ensured that the branch 154 is directed toward the artery 102 (guided by the guide wire 3), the graft 150 may be fully deployed or extended/expanded so that it may, if desired, contact the wall of the aorta 101 and thus fix itself thereto. Also, subsequently, an extender graft 156 is positioned (see FIG. 16) stretching from the branch 154 and into the artery 102. This extender graft 156 is positioned using the guide wire 3 which already is positioned in the artery 102.

However, in order for the extender graft 156 to be able to actually cover the part of the vessel wall 31 where the fixing part 2 engaged the blood vessel (which may have been slightly damaged during the procedure), it is necessary to actually remove the fixing part 2 from the guide wire 3 before introducing the extender graft 156.

Figure 16:
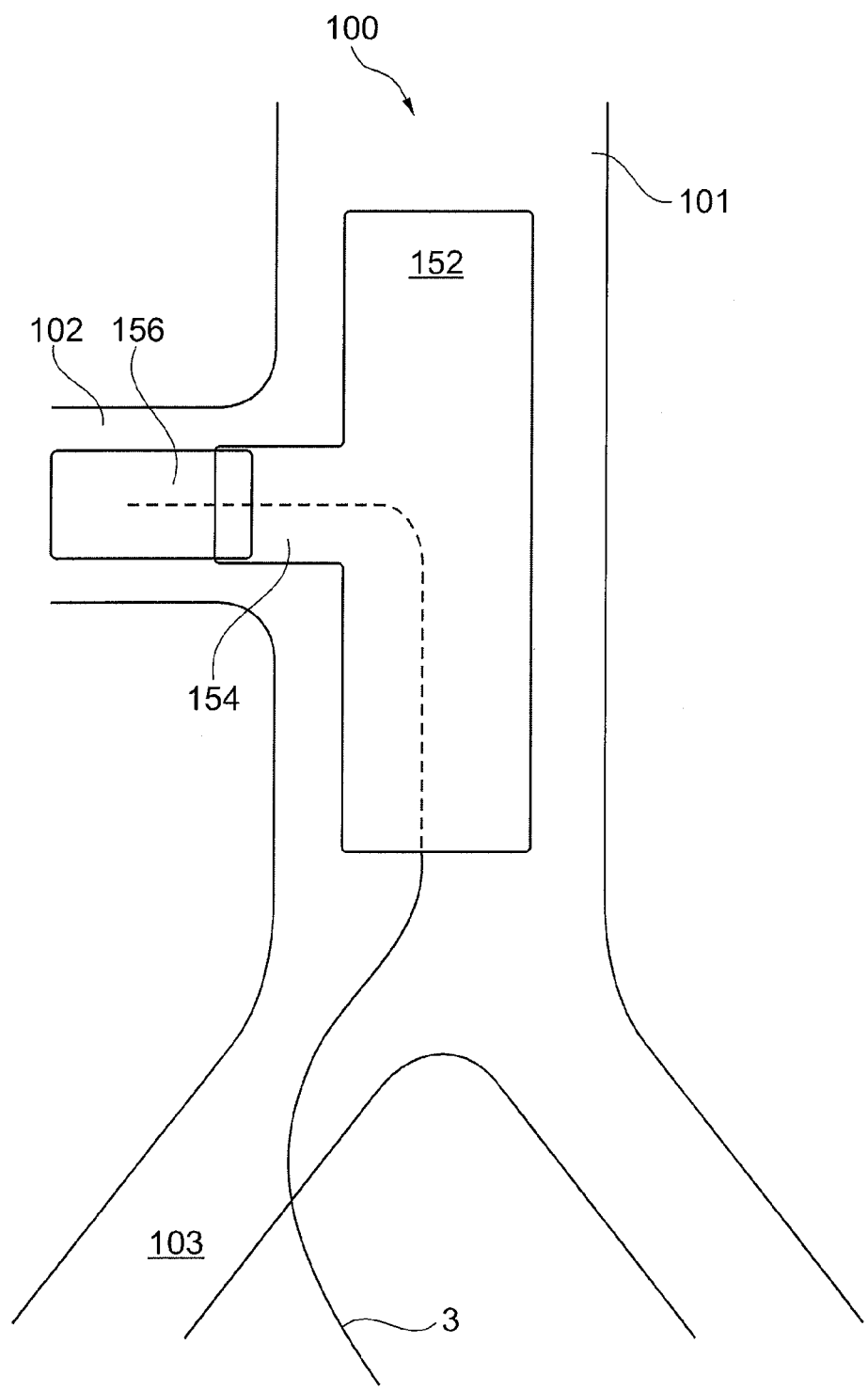

As the fixing part 2 is able to slide along the guide wire 3, this is possible. The fixing part 2 is removed using a delivery catheter as described above, while maintaining the guide wire 3 in place in the artery 102. Having then removed the fixing part 2, the guide wire 3 is subsequently used for introducing the extender graft 156 as illustrated in FIG. 16.

Naturally, more such grafts or grafts with more branches may be used. However, such use and positioning may be performed as described, with the assistance of the use of the fixator and the re-routing of the guide wire 3 using the transport wire 160.

Also, the attachment of the guide wire 3 to the transport wire 160 may be performed within the blood vessel of the person. Such intra corporeal snaring or attachment is a conventional procedure.

Alternatively, the fixators may be guided to the desired vessels along any desired route and from different arteries, such as from the arteries in the arms and legs. Then, when the tubular element has been introduced, guide wires and/or transport wires may be re-routed to allow the desired attaching/snaring, where after the guide wires may extend to the outside of the person through any opening desired. The use of multiple openings at different positions of the person may be desired in order to prevent entanglement of the wires inside the person.

In one situation, the fixator is attached to the guide wire via an attaching wire which has the function of placing the fixator in the target vessel and retrieving it at the end of the procedure before placing the stentgraft connection from the main graft 150 to the target vessel.

The fixing part of the fixator according to the embodiments above may be provided in different sizes, e.g. 5, 6, 7, 8, 9, 10, 11, 12, 13 14 mm in diameter, or fractions thereof, for use in arteries of corresponding diameter. The collapsed fixing part 2 diameter is typically 8 French (2.67 mm diameter on the French catheter scale), and may vary from about 6 to about 12 French (about 2 to about 4 mm), including sizes of 6, 7, 8, 9, 10, 11, 12 French and half sizes there between, depending on the diameter of the delivery catheter to be used to house the fixing part. The size of the delivery catheter is accordingly also from about 6 to about 12 French (about 2 to about 4 mm), including sizes of 6, 7, 8, 9, 10, 11, 12 French and half sizes there between. The retrieving catheter has a size that allows it to fit outside the guide wire and inside the delivery catheter, e.g. from about 3 to about 10 French (about 1 to about 3.3 mm), including sizes of 3, 4, 5, 6, 7, 8, 9, 10 French and half sizes there between. Usually, the guide wire and/or the hypotube guide wire is very pliable and usually have a hydrophilic surface allowing catheterization of narrow, stenotic arteries without damage to the target vessel.

One embodiment of the fixator may be one made of 40 braided 100 μm diameter Nitinol wires provided as a, when compacted, 40 mm long element which may be used in e.g. 5-7 mm blood vessels. When expanded in a 5 mm blood vessel, this fixator will occlude about 58% of the blood vessel cross sectional area, and the openings seen by the blood when flowing through the fixator will be 0.015-0.18 mm$^2$, whereas the occluding percentage in a 7 mm blood vessel is about 47% and the openings 0.06-0.25 mm$^2$.

It is noted that the branched graft 150 may be replaced by a so-called fenestrated graft which has not branch(es) 154 but merely a side opening. The positioning is similar in that the guide wire will extend from the fixator 2 through the side opening and out through the graft 150 as described.

In that situation, the extender graft 156 may also be used, where it may be desired to use a flairing graft having a larger diameter within the lumen 152 so as to ensure that the extender graft is fixed to the graft 150 and is not allowed to release itself therefrom and move into the vessel 102.

Naturally, the graft 150 may have any number of branches 154 or side openings, and even a combination of one or more branches 154 and side openings

The invention claimed is:

1. A method of positioning a tubular element comprising:
providing a tubular element having
a main tube having an inner space defined between a first and a second end portion along a longitudinal axis of the main tube and at least an end opening at the first end portion from the inner space to surroundings of the main tube,
a side opening positioned between the first and second end portions between the inner space and the surroundings,
a transport wire having a first part, which extends from the inner space and out of the tubular element through the end opening, and a second part, which extends from the inner space and out of the tubular element through the side opening,
in a main blood vessel, having a branch vessel, of a patient;
providing an assembly having a guide wire and a fixator adapted to be releasably attached to an inner side of the branch vessel, the fixator being attached to the guide wire, which guide wire has a distal end for introduction into the branch vessel and a proximal end,
introducing the fixator into the branch vessel, via the main blood vessel, and fixing the fixator to the branch vessel,
providing the tubular element inside the main blood vessel so that the first part of the transport wire is engageable from outside the patient,
fixing or attaching the second part of the transport wire to the guide wire and
pulling the first part of the transport wire to have the guide wire extend from the fixator through the side opening, the inner space, and the end opening,
wherein the patient is a person or an animal.

2. A method according to claim 1, wherein:
the tubular element comprises a branch tube attached to the main tube and opening into the main tube, the side opening being an opening from the surroundings into the branch tube, and
the second part of the transport wire extends from the inner space of the main tube and out of the tubular element through the branch tube and the side opening.

3. A method according to claim 1, wherein pulling the first part of the transport wire comprises having the guide wire finally extend to the outside of the patient.

4. A method according to claim 1, wherein:
introducing the fixator comprises having the guide wire of the fixed fixator extend to the outside of the patient,
providing the tubular element comprises having the second part of the transport wire extend to the outside of the patient; and
fixing or attaching the second part to the guide wire outside the patient.

5. A method according to claim 1, wherein fixing or attaching the second part of the transport wire comprises fixing or attaching the second part to the guide wire inside a blood vessel of the patient.

6. A method according to claim 1, wherein providing the assembly comprises providing an assembly in which the fixator may move independently of the guide wire, the assembly further comprising a stopper for preventing the fixator from travelling distally of the stopper or beyond the distal end of the guide wire,
subsequent to pulling the first part of the transport wire, the method further comprising:
removing the fixator while maintaining the distal end of the guide wire inside the branch vessel, and
introducing another element along the guide wire.

7. A method according to claim 6, wherein introducing the fixator comprises introducing another tubular element along the guide wire and positioning the another tubular element to extend from inside the tubular element and into the branch vessel.

8. A method according to claim 7, wherein positioning the another tubular element comprises positioning the another tubular element to cover an area of the branch vessel where the fixator was fixed.

9. A method according to claim 1, wherein the main blood vessel has a plurality of branch vessels,
wherein the tubular element has:
a plurality of side openings,
a plurality of transport wires, the first part of all transport wires extending from the inner space of the main tube and out of the tubular element through the end opening and the second part of each transport wire extending from the inner space of the main tube and out of the tubular element through a separate side opening,
wherein the method further comprises:
providing at least one assembly,
introducing a fixator into each of the branch vessels and fixing each fixator in the plurality of branch vessels,
fixing or attaching each guide wire to a second part of a separate transport wire, where the branch vessel in which the guide wire is fixed corresponds to the side opening through which the second part extends, and
pulling the first parts of the transport wires to have the guide wires extend from the individual fixators through the individual side openings and the inner space of the main tube, the end opening, and toward the outside of the patient.

10. A method according to claim 1, wherein introducing the fixator comprises introducing the fixator into a blood vessel of a patient through a percutaneous opening into the blood vessel, and wherein providing the tubular element inside the main blood vessel comprises provision through the same opening of the patient.

11. A method according to claim 1, comprising:
introducing the tubular element in a fully or partly collapsed state, positioning the tubular element within the main blood vessel, wherein the method further comprises bringing the tubular element from the fully or partly collapsed state and to a fully deployed state pursuant to positioning the tubular element.

12. A method according to claim 1, comprising the step of leaving the tubular element in the patient.

* * * * *